US00PP24626P3

(12) United States Plant Patent
Khemakongkanond

(10) Patent No.: US PP24,626 P3
(45) Date of Patent: Jul. 8, 2014

(54) *AGLAONEMA* PLANT NAMED 'KKAG1201'

(50) Latin Name: ***Aglaonema* hybrid**
Varietal Denomination: KKAG1201

(76) Inventor: Kanchana Khemakongkanond, Bangkok (TH)

( * ) Notice: Subject to any disclaimer, the term of this patent is extended or adjusted under 35 U.S.C. 154(b) by 78 days.

(21) Appl. No.: 13/573,426

(22) Filed: Sep. 14, 2012

(65) Prior Publication Data

US 2014/0082799 P1 Mar. 20, 2014

(51) Int. Cl.
*A01H 5/00* (2006.01)

(52) U.S. Cl.
USPC ..... Plt./376

(58) Field of Classification Search
USPC ..... Plt./376
See application file for complete search history.

*Primary Examiner* — Annette Para
(74) *Attorney, Agent, or Firm* — Cassandra Bright

(57) ABSTRACT

A new and distinct *Aglaonema* cultivar named 'KKAG1201' is disclosed, characterized by strong growth, cream and pink colored foliage with green dots. The new variety is a *Aglaonema*, typically produced as an indoor ornamental plant.

1 Drawing Sheet

Latin name of the genus and species: *Aglaonema* hybrid.
Variety denomination: 'KKAG1201'.

BACKGROUND OF THE INVENTION

This application relates to a new cultivar of *Aglaonema* hybrid. The new variety is the product of a planned breeding program. The new variety originated as a seedling from the open pollination of unnamed, unpatented, *Aglaonema* hybrids, bulk collecting seed and planting the results. The open pollination resulting in the bulk collected seed was organized by the inventor in a research greenhouse in Bangkok, Thailand in 2003.

The new variety was first selected by the inventor, Kanchana Khemakongkanond, a citizen of Thailand, in 2004, in a research greenhouse in Bangkok, Thailand. After identifying the new variety as a potentially interesting selection, the inventor continued confidential testing and propagation of 'KKAG1201', assessing stability of the unique characteristics of this variety.

Asexual reproduction of the new cultivar 'KKAG1201' was first performed at a commercial laboratory in Chonburi, Thailand by tissue culture in January of 2009. Access to all plants was restricted, as plants were kept in a greenhouse not open to the public, and tissue culture plantlets were in a laboratory not accessible to the public. Through subsequent propagation by vegetative cuttings, multiple generations have been reproduced, which have shown that the unique features of this cultivar are stable and reproduced true to type.

SUMMARY OF THE INVENTION

The cultivar 'KKAG1201' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KKAG1201.' These characteristics in combination distinguish 'KKAG1201' as a new and distinct *Aglaonema* cultivar:

1. Strong growth habit.
2. Unique cream, green and pink foliage.

PARENT COMPARISON

Parent varieties are unknown, as seed was bulk collected.

COMMERCIAL COMPARISON

'KKAG1201' is similar in most horticultural characteristics to the unpatented commercial variety *Aglaonema* 'KK9004' in most horticultural characteristics. The new variety, however, produces foliage that is pink and cream with green dots, whereas 'KK9004' produces foliage that is white with green dots. Additionally, the new variety produces wider leaves than 'KK9004'.

BRIEF DESCRIPTION OF THE PHOTOGRAPH

The accompanying photograph in FIG. 1 illustrates in full color a typical plant of 'KKAG1201' grown in a commercial greenhouse in Honslersijk, the Netherlands. This plant is approximately 8 months old, shown planted in an 12 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'KKAG1201' plants grown in a greenhouse in Honslerdijk, the Netherlands. Temperatures ranged between 18° C. to 20° C. at night and 20° C. to 22° C. during the day. No photoperiodic or chemical treatments were given to the plants Measurements and numerical values represent averages of typical plant types.

Botanical classification: *Aglaonema* hybrid 'KKAG1201'.

PROPAGATION

Type of propagation typically used: Side shoot cuttings.

Time to initiate roots: About 14 days at approximately 21° C.

Root description: Moderately dense, moderately thick, non-fibrous, fleshy, not free-branched, color near RHS Greyed-Orange 164C.

Time to produce rooted plantlet: Approximately 10 weeks at approximately 19° to 23° C.

PLANT

Growth habit: Broad upright.

Plant shape: Ovate.

Height: Approximately 29.5 cm to top of highest leaf.

Plant spread: Approximately 28.3 cm in a 12 cm circular pot.

Normal pot size: 12 cm pot.

Growth rate: Moderate.

Stem:

*Diameter.*—7 mm.

*Length.*—5.0 cm.

*Color.*—Near RHS 146A.

*Texture.*—Smooth, moderately glossy.

Branching characteristics: Basal clumping (branching), no lateral branches.

Number of clumps of leaves: 2.

Number of leaves per clump: Average 10.

Number of leaves per plant: Approximately 20.

Age of plant described: Approximately 8 months.

FOLIAGE

Leaf:

*Arrangement.*—Irregular spiral.

*Average length (excluding petiole).*—Approximately 14.2 cm.

*Average width.*—Approximately 8.5 cm.

*Shape of blade.*—Ovate.

*Aspect.*—Leaves upright to slightly outward.

*Apex.*—Apiculate.

*Base.*—Rounded to short attenuate.

*Margin.*—Entire, undulate.

*Texture of top surface.*—Smooth, moderately glossy.

*Texture of bottom surface.*—Smooth, slightly glossy.

*Color.*—Young foliage upper side: Near RHS 51B, tinged near RHS 150D towards the base, dotted throughout near RHS 144B, 144C and 139A. Margin also colored near 144B, 144C and 139A. Young foliage under side: Near RHS Red 49A, Base near 49D dotted and margin colored near RHS N137A. Mature foliage upper side: Near RHS 161B, tinged near RHS 49C towards the tip, moderately dotted and margin coloration near RHS N137A, 139A and 143A. Mature foliage under side: Near RHS Greyed-Yellow 160C and 161C, moderately dotted and margin coloration near RHS 137A and N137A.

Venation:

*Type.*—Pinnate.

*Venation coloration upper side.*—Near RHS Yellow-Green 145B.

*Venation coloration under side.*—Near RHS Yellow-Green 146B.

Sheath:

*Average length.*—Approximately 5.9 cm.

*Average width.*—Approximately 0.3 cm.

*Color.*—Near RHS Green 143C.

*Texture.*—Smooth, moderately glossy.

Petiole:

*Length.*—Approximately 9.7 cm.

*Width.*—At distal end: Approximately 0.3 cm. Above clump: Approximately 0.5 cm.

*Color.*—Near RHS Yellow-Green 146A.

*Strength.*—Strong.

Geniculum: No geniculum visible.

FLOWERING CHARACTERISTICS

Flowers not observed to date.

OTHER CHARACTERISTICS

Disease resistance: Neither resistance nor susceptibility to the normal diseases found in *Aglaonema* has been observed.

Drought tolerance and cold tolerance: Tender, indoor plant susceptible to cold and drought.

Fruit/seed production: No fruits/seeds detected to date.

What is claimed is:

1. A new and distinct cultivar of *Aglaonema* plant named 'KKAG1201' as herein illustrated and described.

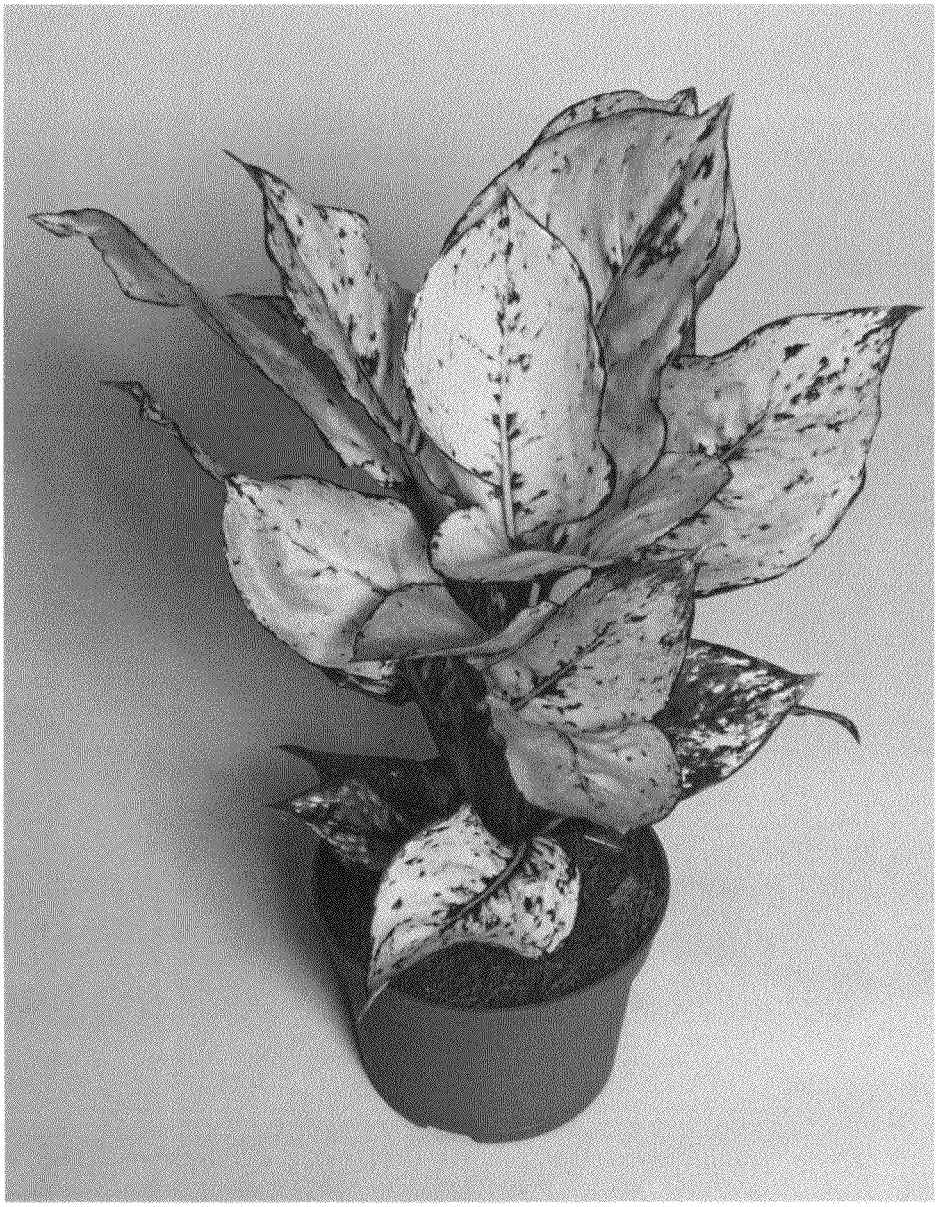

* * * * *